(12) United States Patent
Koike et al.

(10) Patent No.: US 7,335,785 B2
(45) Date of Patent: Feb. 26, 2008

(54) ACETYLENE ALCOHOLS HAVING A FLUOROALKYL GROUP AND METHODS FOR PREPARING THE SAME

(75) Inventors: Noriyuki Koike, Takasaki (JP); Yasunori Sakano, Annaka (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 242 days.

(21) Appl. No.: 11/144,646

(22) Filed: Jun. 6, 2005

(65) Prior Publication Data

US 2005/0272948 A1 Dec. 8, 2005

(30) Foreign Application Priority Data

Jun. 7, 2004 (JP) .............................. 2004-168082
Aug. 20, 2004 (JP) .............................. 2004-240524

(51) Int. Cl.
*C07F 7/18* (2006.01)

(52) U.S. Cl. .................................................... 556/482

(58) Field of Classification Search ..................... None
See application file for complete search history.

(56) References Cited

U.S. PATENT DOCUMENTS 6,114,562 A 9/2000 Fukuda et al.
7,067,688 B2 * 6/2006 Koike et al. ................ 556/482

FOREIGN PATENT DOCUMENTS

| EP | 0622420 A1 | 4/1994 |
| EP | 0982312 A1 | 3/2000 |
| JP | 2000-53685 A | 2/2000 |

OTHER PUBLICATIONS

Chemical Abstract: 2005:1293659, 2005, rn=717825-76-8.*
Database Registry Online, Chemical Abstracts Service, Ohio, US, Jul. 2004, XP002343670, (abstract), p. 1.
Database CA Online, Chemical Abstracts Service, Ohio, US, Nakatani et al., XP-002343669, (abstract), p. 4.

* cited by examiner

*Primary Examiner*—Samuel A Barts
(74) *Attorney, Agent, or Firm*—Birch, Stewart, Kolasch & Birch, LLP

(57) ABSTRACT

A fluorine-containing acetylene alcohol represented by the following formula (1),

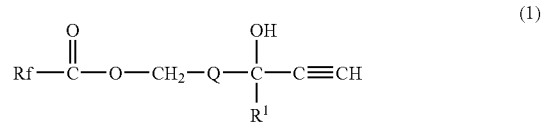

wherein Rf is a linear or branched perfluoroalkyl group having 3 to 100 carbon atoms and may have an ether bond, —C—O—C—, Q is a divalent hydrocarbon group having 1 to 6 carbon atoms, and R1 is an alkyl group having 1 to 4 carbon atoms.

4 Claims, 4 Drawing Sheets

ACETYLENE ALCOHOLS HAVING A FLUOROALKYL GROUP AND METHODS FOR PREPARING THE SAME

CROSS REFERENCES

This application claims benefits of Japanese Patent application No. 2004-168082 filed on Jun. 7, 2004, and Japanese Patent application No. 2004-240524 filed on Aug. 20, 2004, the contents of which are hereby incorporated by reference.

FIELD OF THE INVENTION

The present invention relates to novel acetylene alcohols each having a fluoroalkyl group and methods for preparing the same.

DESCRIPTION OF THE PRIOR ART

There are commercially available acetylene alcohols. For example, 3-methyl-1-butyne-3-ol, 3-methyl-1-pentyne-3-ol, 2,5-dimethyl-3-hexyne-2,5-diol are sold under the trade name, Olfine, from Nisshin Chemical Industry Co., and acetylene glycols are sold under the trade name, Surfynol, from Air Products and Chemicals, Inc.

These acetylene alcohols are industrially very important compounds having various uses, for example, as intermediates for chemical synthesis; nonionic surfactants such as metal surface treatment agents, low-foaming wetting agents, antifoaming agents, or pigment dispersants; and retarders for hydrosilylation reaction on account of their high tendency to form complexes with transition metals, as described in Japanese Patent Publication S44-31476, Japanese Patent Application Laid-Open No. H6-329917 and Japanese Patent Application Laid-Open No. H9-143371.

However, when the acetylene alcohols are used in a reaction system containing a highly fluorinated compound, a desired effect is not attained sometimes due to difference in specific gravity from the fluorinate compound or low solubility in the fluorinate compound. For example, when the aforesaid commercially available acetylene alcohols are used as retarders for a curing reaction of highly fluorinated polymers through hydrosilylation, cured products may have defects because of non-uniformity of the curing reaction due to poor compatibility of the acetylene alcohols with the polymer.

Meanwhile, Japanese Patent Application Laid-Open No. 2000-53685 discloses a fluorinated organosilicon compound prepared by reacting an acetylene alcohol with a chlorosilane having a fluoroalkyl group. The fluorinated organosilicon compound dissolves readily in fluorosilicones or perfluoro polymers, so that this has been used to retard hydrosilylation reaction of these highly fluorinated substances. However, its performance as a retarder of the fluorinated organosilicon compound needs to be improved.

SUMMARY OF THE INVENTION

After extensive studies, the present inventors have found that the poor performance of the fluorinated organosilicon compound is due to a fact that a hydroxyl group on the α-carbon, i.e., the carbon atom bonded to the ethynyl group, is silylated.

Therefore, an object of the present invention is to provide a novel acetylene alcohol which has a floroalkyl group and whose hydroxy group on α-carbon atom is not silylated.

The first aspect of the present invention is a fluorine-containing acetylene alcohol represented by the following formula (1), $$Rf-\underset{\parallel}{\overset{O}{C}}-O-CH_2-Q-\underset{R^1}{\overset{OH}{\underset{|}{C}}}-C\equiv CH \quad (1)$$

wherein Rf is a linear or branched perfluoroalkyl group having 3 to 100 carbon atoms and may have an ether bond, —C—O—C—, Q is a divalent hydrocarbon group having 1 to 6 carbon atoms, and $R^1$ is an alkyl group having 1 to 4 carbon atoms.

The second aspect of the present invention is a fluorine-containing acetylene alcohol represented by the following formula (2), $$Rf-Z-\underset{R^3}{\overset{R^2}{\underset{|}{Si}}}-O-CH_2-Q-\underset{R^1}{\overset{OH}{\underset{|}{C}}}-C\equiv CH \quad (2)$$

wherein Rf and Q are as defied above, $R^1$, $R^2$ and $R^3$ may be the same with or different from each other and represent an alkyl group having 1 to 4 carbon atoms, and Z is a divalent organic group having 1 to 20 carbon atoms.

The fluorine-containing acetylene alcohols of the present invention are extremely useful as retarder for hydrosilylation curing reaction of highly fluorinated polymers. They can also be useful as nonionic surfactants and intermediates for chemical synthesis.

DETAILED DESCRIPTION OF THE PREFERRED EMBODIMENTS

Figure 1:
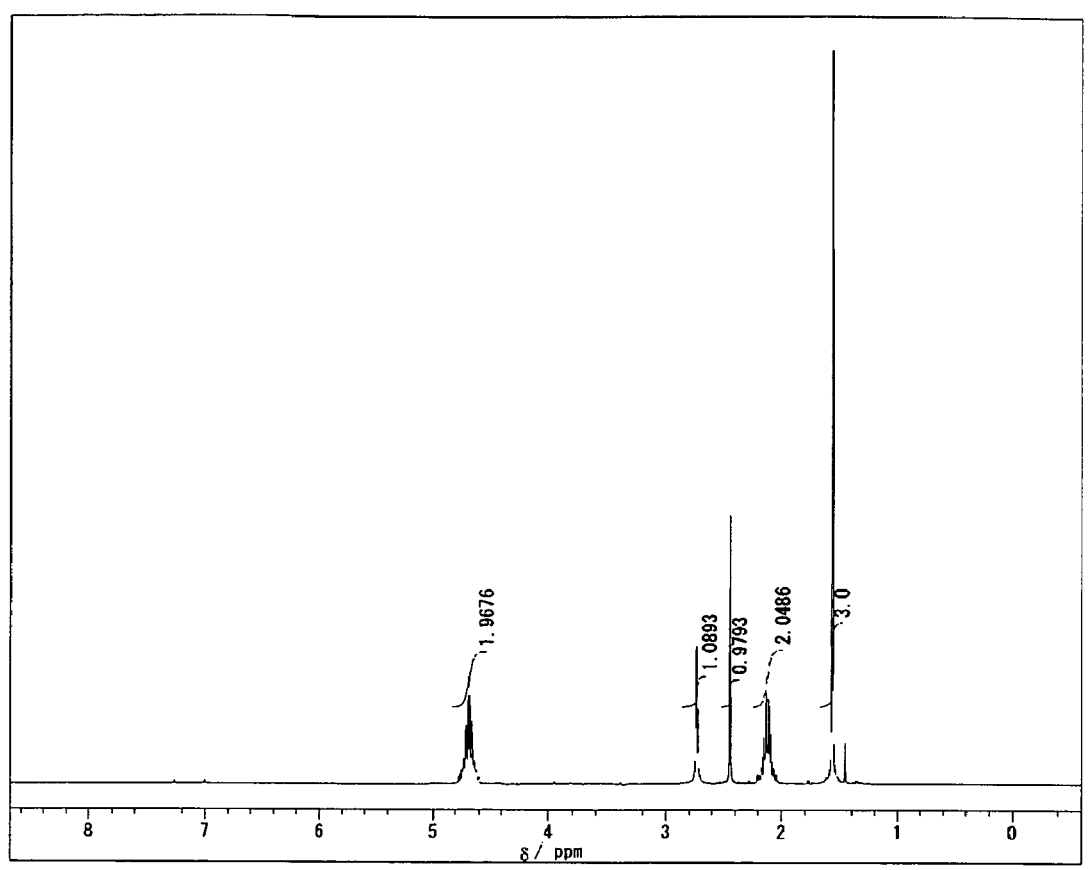
FIG. 1 is a $^1$H-NMR chart of the present acetylene alcohol prepared in Example 1.

In the fluorine-containing acetylene alcohol represented by the aforesaid formula (1) or (2), Rf is a linear or branched perfluoroalkyl group having 3 to 100 carbon atoms and may have an ether bond, —C—O—C—.

Examples of Rf are as follows.

n = 3-10

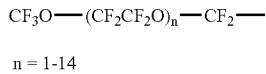

n = 1-14

n = 0-13

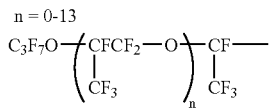

n = 0-30

$C_3F_7O-(CF_2CF_2CF_2O)_n-CF_2CF_2-$ n = 0-8

$CF_3O-(CF_2CF_2O)_n(CF_2O)_m-CF_2-$ n and m are integers not smaller than 1, with 2n + m being not greater than 30.

Q is a divalent hydrocarbon group having 1 to 6 carbon atoms, for example, methylene, ethylene, n-porpylene, n-butylene, isobutylene, and phenylene groups, among which an ethylene group is preferred.

$R^1$, $R^2$, and $R^3$ may be the same with or different from each other. Each of $R^1$, $R^2$, and $R^3$ is an alkyl group having 1 to 4 carbon atoms, for example, methyl, ethyl, n-propyl, isopropyl, n-butyl, isobutyl, and t-butyl groups. Preferably, $R^1$ is a methyl group.

Z is a divalent organic group having 1 to 20 carbon atoms. Z may have oxygen atoms, nitrogen atoms, and carbonyl groups at positions other than the terminal thereof. Examples of Z are as follows:

$-(CH_2)_p-$ wherein p is an integer of from 1 to 10, preferably 2 to 4;

$-CH_2-O-(CH_2)_q-$ wherein q is an integer of from 1 to 9, preferably 2 to 4;

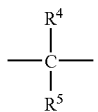

wherein $R^4$ and $R^5$ may be the same with or different from each other and are selected from the group consisting of a hydrogen atom and alkyl groups having 1 to 9 carbon atoms, for example, methyl, ethyl, propyl, phenyl, and cyclohexyl groups; and

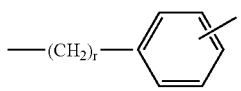 r = 0-4

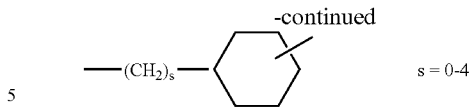 s = 0-4

Preparation Methods

The fluorine-containing acetylene alcohol represented by the formula (1) may be prepared by reacting an acid halide represented by the formula (3),

 (3)

wherein Rf is as defined above and X is a halogen atom, with a hydroxy acetylene alcohol represented by the following formula (4),

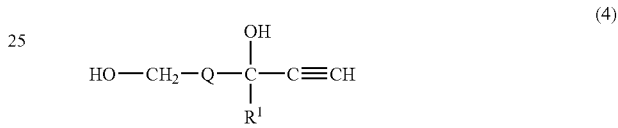 (4)

wherein Q and $R^1$ are as defined above, which has two hydroxyl groups, one bonded to the tertiary carbon atom to which the acetylene group is bonded and one bonded to a primary carbon atom.

In the reaction, only the latter hydroxyl group is converted to an ester bond to form the fluorine-containing acetylene alcohol represented by the formula (1),

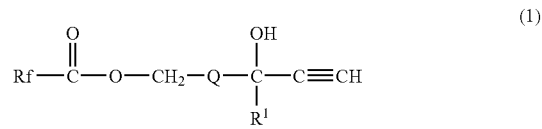 (1)

wherein Rf, Q and $R^1$ are as defined above, while the former bonded to the tertiary carbon remains unreacted.

The fluorine-containing acetylene alcohol represented by the formula (2) may be prepared by reacting the halogenated silicon compound represented by the formula (5),

 (5)

wherein Rf, Z, X, $R^2$ and $R^3$ are as defied above, with the hydroxylacetylene alcohol represented by the aforesaid formula (4).

Similarly to the aforesaid reaction, only the hydroxyl group bonded to the primary carbon atom of the hydroxylacetylene alcohol is converted into a siloxane bond to from the fluorine-containing acetylene alcohol represented by the formula (2),

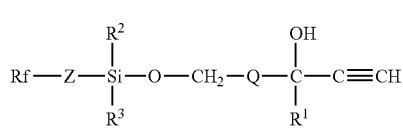

(2)

wherein Rf, Q, R1, R2, R3 are as defined above, while the hydroxyl group bonded to the tertiary carbon atom remains unreacted.

Examples of the hydroxyl acetylene alcohol are as follows.

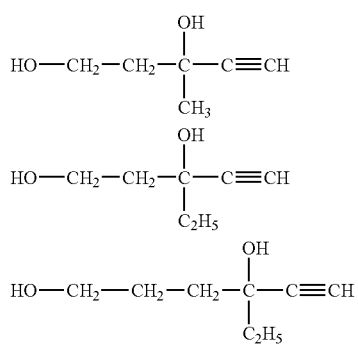

Examples of the acid halide are as follows.

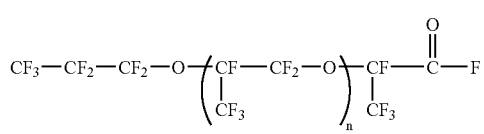

n = 0-30

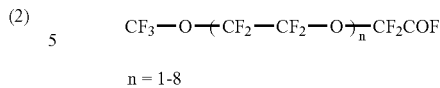

n = 1-8

$C_2F_5-O-(CF_2-CF_2-O)_n-CF_2COF$ n = 1-8

Examples of the halogenated silicon compound are as follows.

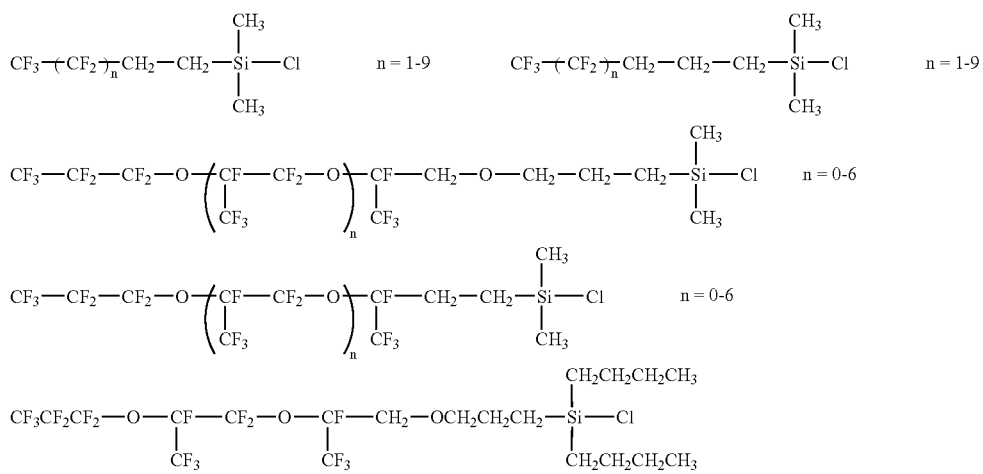

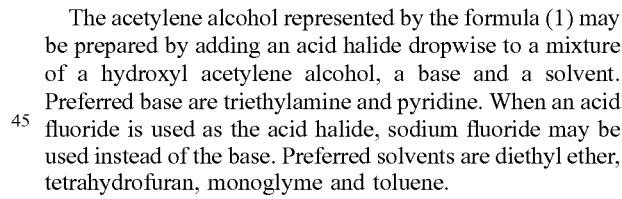

The acetylene alcohol represented by the formula (1) may be prepared by adding an acid halide dropwise to a mixture of a hydroxyl acetylene alcohol, a base and a solvent. Preferred base are triethylamine and pyridine. When an acid fluoride is used as the acid halide, sodium fluoride may be used instead of the base. Preferred solvents are diethyl ether, tetrahydrofuran, monoglyme and toluene.

For one mole of the hydroxyl acetylene alcohol, from 1 to 2 moles of the base and from 0.3 to 1 mol the acid halide are used. The reaction may be carried out at a temperature of from 20 to 50 degrees C. for 30 to 60 minutes. After the reaction completes, the reaction mixture is washed with water to dissolve salts and the organic layer is separated. By distilling the solvent off, the intended acetylene alcohol is obtained.

The acetylene alcohol represented by the formula (2) may be prepared by adding a halogenated silicon compound dropwise to a mixture of a hydroxyl acetylene alcohol, a base and a solvent. Preferred bases are triethylamine and pyridine. Preferred solvents are diethyl ether, tetrahydrofuran, monoglyme and toluene.

For one mole of the hydroxyl acetylene alcohol, from 1 to 2 moles of the base and from 0.4 to 1 mol of the halogenated silicon compound are used. The reaction may be carried out at a temperature of from 20 to 50 degrees C. for 30 to 60 minutes. After the reaction completes, the reaction mixture is poured into an aqueous saturated solution of sodium bicarbonate. The organic layer is separated which is washed with water. By removing the solvent from the organic layer, the intended acetylene alcohol is obtained.

EXAMPLES

The present invention will be further explained in detail with reference to the following Examples, but not limited thereto.

Example 1

In a 100 ml three-necked flask equipped with a stirrer, a condenser, and a thermometer, 1.0 g of 3-methyl-4-pentyne-1,3-diol, 0.8 g of sodium fluoride and 30 ml of diethylether were placed, to which 7.8 g of the compound represented by the formula (6) was added dropwise while stirring.

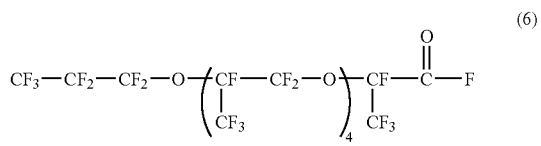
(6)

After the addition completed, the stirring was kept further for 20 minutes. The reaction mixture was filtered to remove a solid substance. The filtrate was repeatedly washed with water. The resultant organic phase was stripped at a temperature of 70 degrees C. and a pressure of 10 mmHg to remove the solvent. Transparent pale yellow liquid weighing 7.3 g was obtained.

This was analyzed by $^1$H-NMR and IR. FIG. 1 shows $^1$H-NMR spectrum of the product dissolved in CDCl$_3$. The peaks observed are listed below with assignment, integrated peak area, and multiplicity shown in parentheses.

$^1$H-NMR spectrum (CDCl$_3$) δ1.56(—C$\underline{H}_3$, 3H, s) δ2.13 (—OCH$_2$C$\underline{H}_2$—, 2H, m) δ2.45(—C≡C$\underline{H}$, 1H, m) δ2.73 (—O$\underline{H}$, 1H, s) δ4.68(—OC$\underline{H}_2$CH$_2$—, 2H, m)

Figure 2:
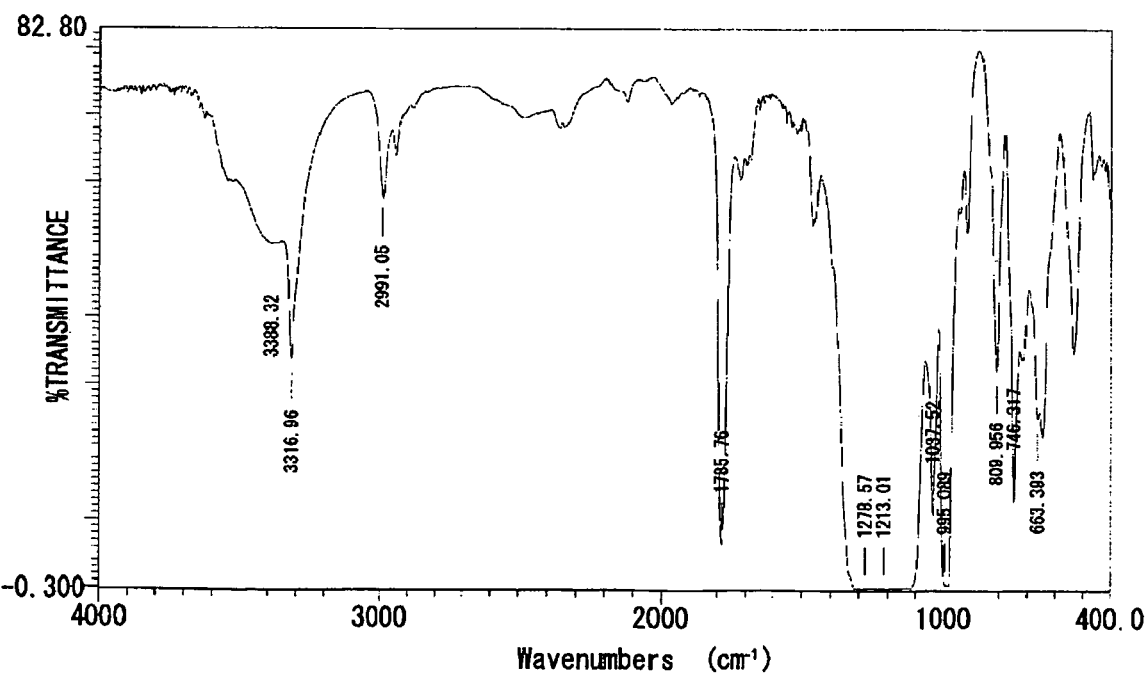
FIG. 2 is an IR chart of the present acetylene alcohol prepared in Example 1.

FIG. 2 shows an IR spectrum of the product. The absorption bands observed are listed below with assignment shown in parentheses.

3388 cm$^{-1}$ (—OH)
3316 cm$^{-1}$ (—C≡CH)
1785 cm$^{-1}$ (C═O)
1400-1000 cm$^{-1}$ (C—F)

Based on the spectral analyses shown above, it was confirmed that the reaction product had the structure represented by the following formula (7).

Example 2

In a 100 ml three-necked flask equipped with a stirrer, a condenser, and a thermometer, 1.0 g of 3-methyl-4-pentyne-1,3-diol, 0.9 g of triethylamine and 30 ml of diethylether were placed, to which 4.3 g of the halogenated silicon compound represented by the following formula was added dropwise while stirring.

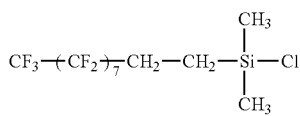

After stirred at room temperature for about 15 minutes, the reaction mixture was poured in a saturated aqueous solution of sodium bicarbonate. The resultant organic layer was separated and then washed with water. Subsequently, the organic layer was stripped of the solvent. Transparent pale yellow liquid weighing 4.2 g was obtained.

Figure 3:
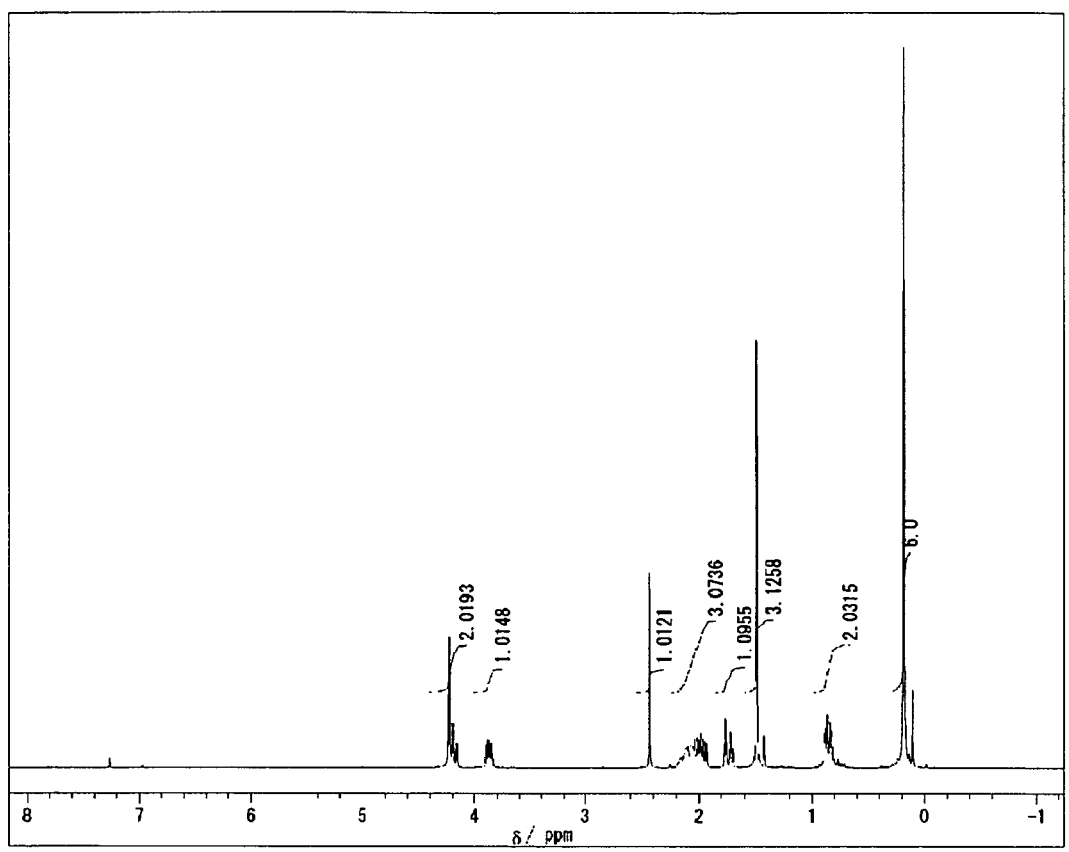
FIG. 3 is a $^1$H-NMR chart of the present acetylene alcohol prepared in Example 2.

This was analyzed by $^1$H-NMR and IR. FIG. 3 shows a $^1$H-NMR spectrum of the product dissolved in CDCl$_3$. The peaks observed are listed below with assignment, integrated peak area, and multiplicity shown in parentheses.

$^1$H-NMR (CDCl$_3$) δ0.18(Si—C$\underline{H}_3$, 6H, s) δ0.85(—C$\underline{H}_2$—Si, 2H, m) δ1.49(—C$\underline{H}_3$, 2H, m) δ1.73(—OCH$_2$C$\underline{H}_2$—, 1H, m) δ1.98(—OCH$_2$C$\underline{H}_2$—, 1H, m) δ2.09(—CF$_2$C$\underline{H}_2$—, 2H, m) δ2.43(—C≡C$\underline{H}$, 1H, s) δ3.86(—OC$\underline{H}_2$CH$_2$—, 1H, m) δ4.18(—OC$\underline{H}_2$CH$_2$—, 1H, m) δ4.23(—O$\underline{H}$, 1H, s)

Figure 4:
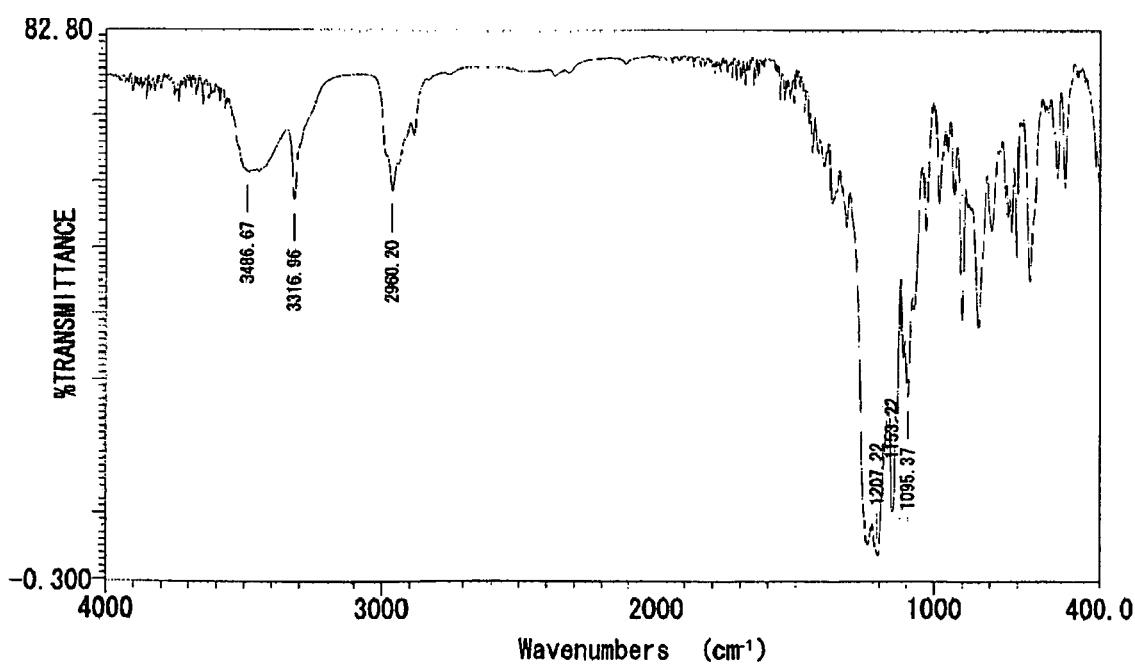
FIG. 4 is an IR chart of the present acetylene alcohol prepared in Example 2.

FIG. 4 shows an IR spectrum of the product. The absorption bands observed are listed below with assignment shown in parentheses.

3486 cm$^{-1}$ (—OH)
3316 cm$^{-1}$ (—C≡CH)
1300-1000 cm$^{-1}$ (C—F)

Based on the spectral analyses shown above, it was confirmed that the reaction product had the structure represented by the following formula (8).

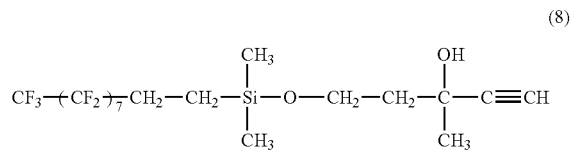
(8)

Example 3

In a 100 ml three-necked flask equipped with a stirrer, a condenser, and a thermometer, 2.5 g of 3-methyl-4-pentyne-

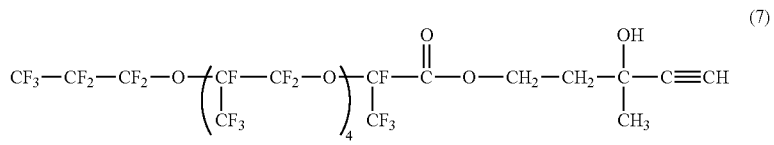
(7)

1,3-diol, 1.2 g of sodium fluoride and 50 ml of diethylether were placed, to which 30 g of a compound represented by the formula was added dropwise while stirring.

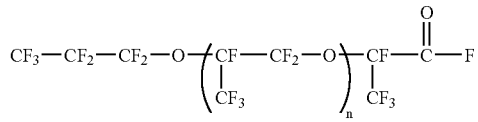

n = 23 (average)

After the addition completed, the stirring was kept further for about 1 hr. The reaction mixture was filtered to remove a solid substance. The filtrate was repeatedly washed with water and then stripped at a temperature of 70 degrees C. and a pressure of 10 mmHg to remove the solvent. Transparent pale yellow liquid weighing 28 g was obtained.

Figure 5:
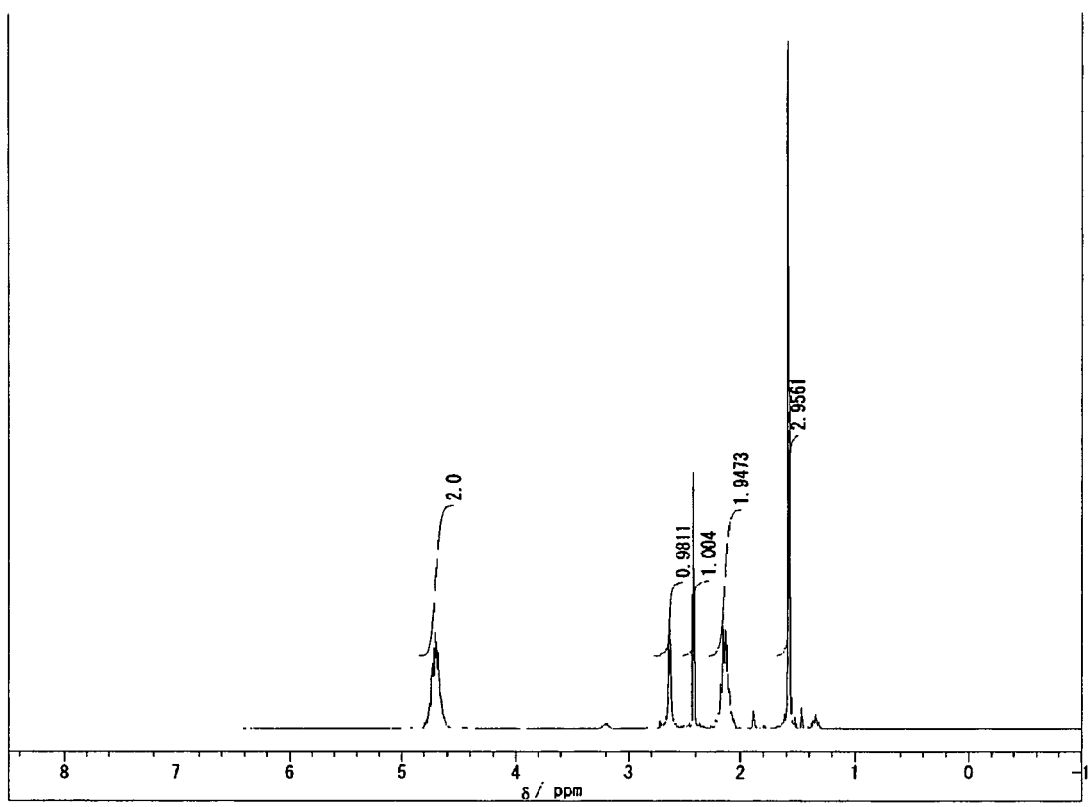
FIG. 5 is a $^1$H-NMR chart of the present acetylene alcohol prepared in Example 3.

This was analyzed by $^1$H-NMR and IR. FIG. 5 shows a $^1$H-NMR spectrum of the product dissolved in CDCl$_3$. The peaks observed are listed below with assignment, integrated peak area, and multiplicity shown in parentheses.

$^1$H-NMR (CDCl$_3$) δ1.57(—C$\underline{H}_3$, 3H, s) δ2.12(—OCH$_2$C$\underline{H}_2$—, 2H, m) δ2.41(—C≡C$\underline{H}$, 1H, m) δ2.64(—O$\underline{H}$, 1H, s) δ4.69(—OC$\underline{H}_2$CH$_2$—, 2H, m)

Figure 6:
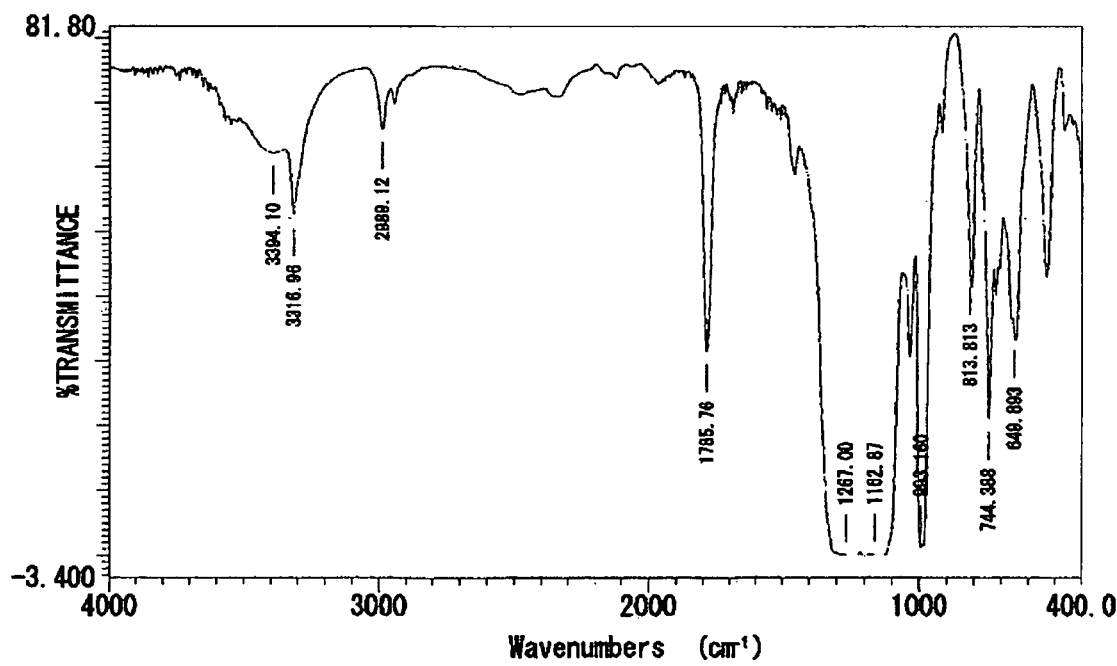
FIG. 6 is an IR chart of the present acetylene alcohol prepared in Example 3.

FIG. 6 shows an IR spectrum of the product. The absorption bands observed are listed below with assignment shown in parentheses.

3394 cm$^{-1}$ (—OH)
3316 cm$^{-1}$ (—C≡CH)
1785 cm$^{-1}$ (C═O)
1400-1000 cm$^{-1}$ (C—F)

Based on the spectral analyses shown above, it was confirmed that the reaction product had the structure represented by the following formula.

Example 4

In a 100 ml three-necked flask equipped with a stirrer, a condenser, and a thermometer, 6.8 g of 3-methyl-4-pentyne-1,3-diol, 5.5 g of triethylamine and 50 ml of toluene were placed, to which 35 g of the halogenated silicon compound represented by the following formula was added dropwise while stirring.

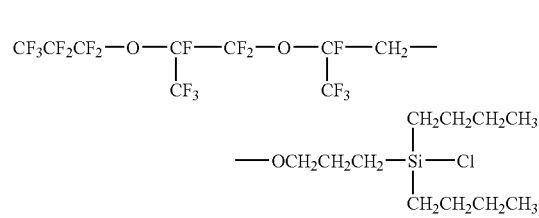

After stirred for about 4 hours at room temperature, the reaction mixture was poured in water. The resultant organic layer was separated. Subsequently, the organic layer was washed with water and stripped of the solvent. A condensate obtained was distilled at a pressure of 1 mmHg and 28.8 g of a fraction at a temperature range of from 146 to 152 degrees C. was obtained.

Figure 7:
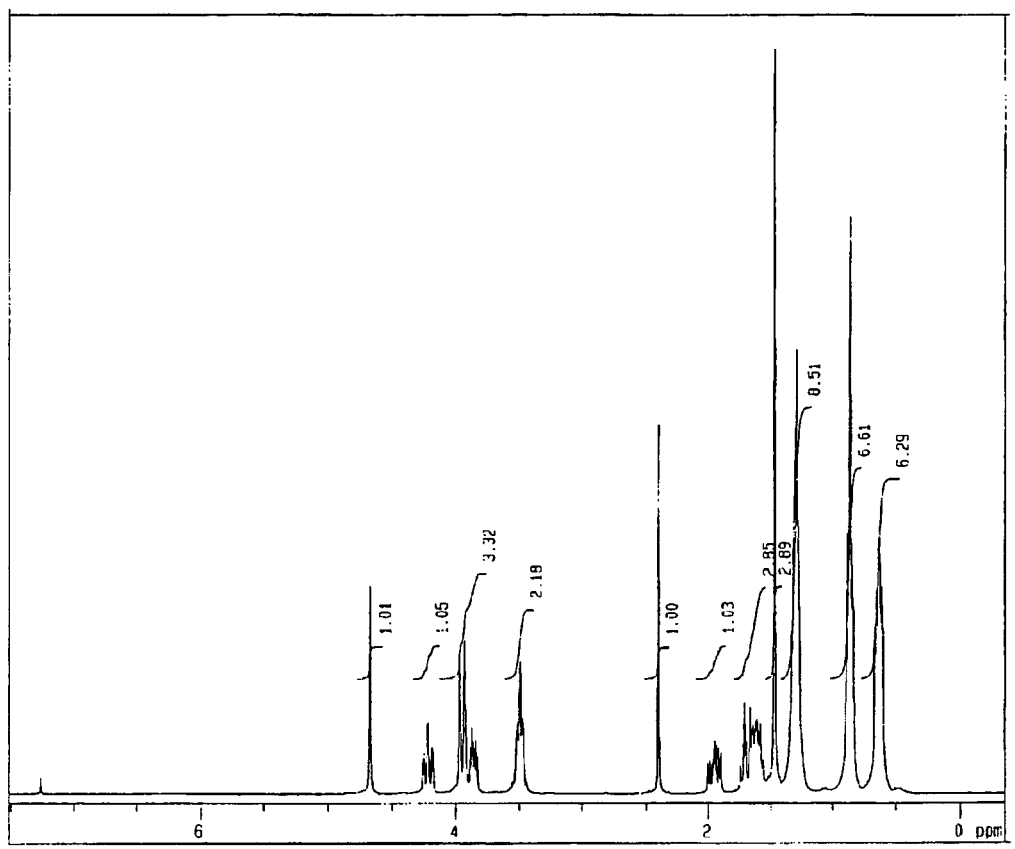
FIG. 7 is a $^1$H-NMR chart of the present acetylene alcohol prepared in Example 4.

FIG. 7 shows a $^1$H-NMR spectrum of the fraction dissolved in CDCl$_3$. The peaks observed are listed below with assignment, integrated peak area, and multiplicity shown in parentheses.

$^1$H-NMR (CDCl$_3$) δ0.62(Si—C$\underline{H}_2$, 6H, s) δ0.86(C$\underline{H}_3$—CH$_2$—CH$_2$—CH$_2$—Si, 6H, m) δ1.30(CH$_3$—C$\underline{H}_2$—C$\underline{H}_2$—CH$_2$—Si, 8H, m) δ1.47(C$\underline{H}_3$—C—OH, 3H, s) δ1.62(—OCH$_2$—C$\underline{H}_2$—CH$_2$, 2H, m) δ1.71(—OCH$_2$C$\underline{H}_2$—, 1H, m) δ1.95(—OCH$_2$C$\underline{H}_2$—, 1H, m) δ2.40(—C≡C$\underline{H}$, 1H, s) δ3.49(—OC$\underline{H}_2$—CH$_2$—CH$_2$, 2H, d) δ3.94(CF—CH$_2$—O, 2H, d) δ3.85(—OC$\underline{H}_2$CH$_2$—, 1H, m) δ4.21(—OC$\underline{H}_2$CH$_2$—, 1H, m) δ4.67(—O$\underline{H}$, 1H, s)

Figure 8:
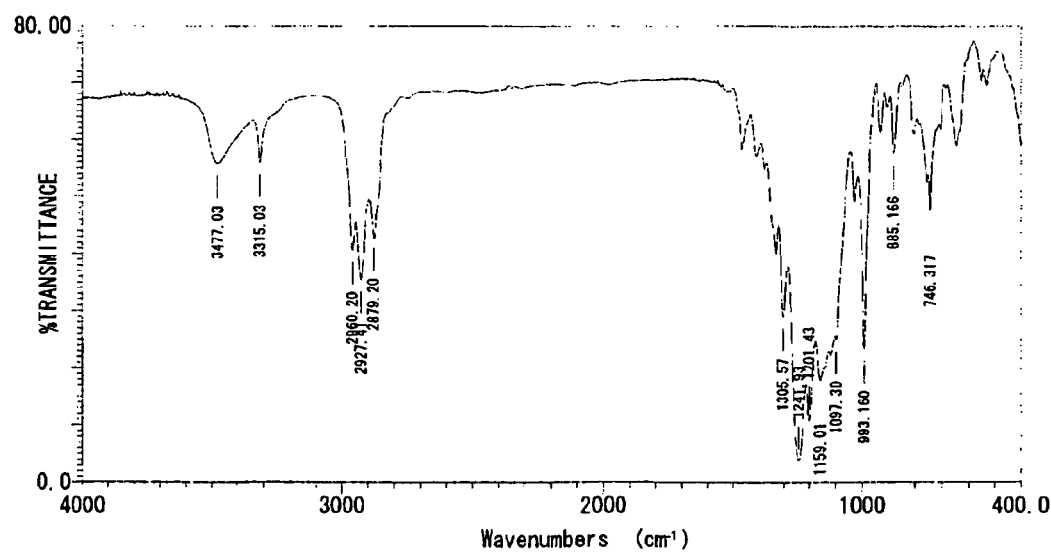
FIG. 8 is an IR chart of the present acetylene alcohol prepared in Example 4.

FIG. 8 shows an IR spectrum of the fraction. The absorption bands observed are listed below with assignment shown in the parentheses.

3477 cm$^{-1}$ (—OH)
3315 cm$^{-1}$ (—C≡CH)
2960, 2927, 2879 cm$^{-1}$ (C—H)
1300~1000 cm$^{-1}$ (C—F)

Based on the spectral analyses, it was confirmed that the compound having the structure of the formula (10) was produced.

(9)

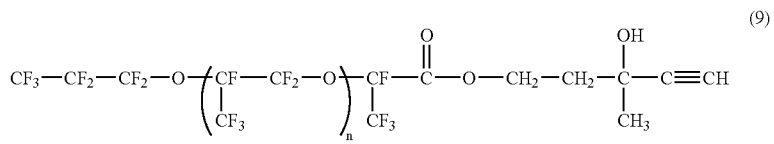

n = 23 (average)

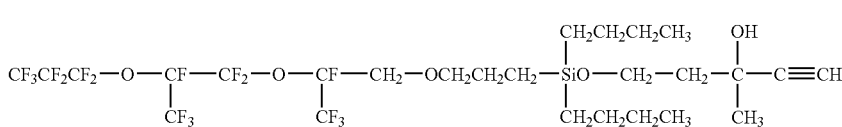

(10)

The invention claimed is:

1. A fluorine-containing acetylene alcohol represented by the following formula (1),

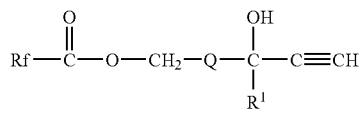

(1)

wherein Rf is a linear or branched perfluoroalkyl group having 3 to 100 carbon atoms and may have an ether bond, —C—O—C—, Q is a divalent hydrocarbon group having 1 to 6 carbon atoms, and $R^1$ is an alkyl group having 1 to 4 carbon atoms.

2. A fluorine-containing acetylene alcohol represented by the following formula (2),

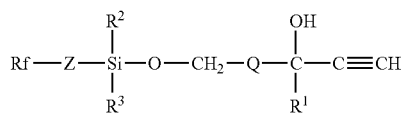

(2)

wherein Rf is a linear or branched perfluoroalkyl group having 3 to 100 carbon atoms and may have an ether bond, —C—O—C—, Q is a divalent hydrocarbon group having 1 to 6 carbon atoms, $R^1$ represents an alkyl group having 1 to 4 carbon atoms, $R^2$ and $R^3$ may be the same with or different from each other and are selected from the group consisting of methyl, ethyl, n-propyl and n-butyl groups, and Z is a divalent organic group having 1 to 20 carbon atoms.

3. A method for preparing the fluorine-containing acetylene alcohol according to claim 1, said method comprising a step of reacting an acid halide represented by the following formula (3),

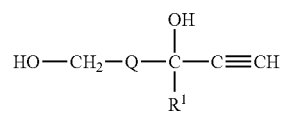

(3)

wherein Rf is as defined above and X is a halogen atom, with a hydroxyl acetylene alcohol represented by the following formula (4),

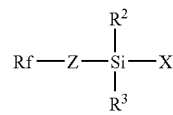

(4)

wherein Q and $R^1$ are as defined above, to form an ester bond.

4. A method for preparing the fluorine-containing acetylene alcohol according to claim 2, said method comprising a step of reacting a halogenated silicon compound represented by the following formula (5),

(5)

wherein Rf, X, Z, $R^2$ and $R^3$ are as defined above, with a hydroxyl acetylene alcohol represented by the following formula (6),

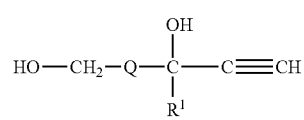

(6)

wherein Q and $R^1$ are as defined above.

* * * * *